US 6,742,929 B2

(12) United States Patent
Horbaschek

(10) Patent No.: US 6,742,929 B2
(45) Date of Patent: Jun. 1, 2004

(54) UNIVERSAL X-RAY DEVICE HAVING A PIVOTALLY MOUNTED RADIATOR AND A DISPLACEABLY MOUNTED DETECTOR

(75) Inventor: Heinz Horbaschek, Erlangen (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

(21) Appl. No.: 10/079,019

(22) Filed: Feb. 19, 2002

(65) Prior Publication Data

US 2002/0118793 A1 Aug. 29, 2002

(30) Foreign Application Priority Data

Feb. 28, 2001 (DE) .......................................... 101 09 754

(51) Int. Cl.[7] .............................................. H05G 1/02
(52) U.S. Cl. ...................... 378/197; 378/195; 378/196
(58) Field of Search ................................ 378/195, 196, 378/197

(56) References Cited

U.S. PATENT DOCUMENTS

| 5,410,584 | A | | 4/1995 | Schaefer et al. ............ 378/196 |
| 5,636,259 | A | * | 6/1997 | Khutoryansky et al. .... 378/197 |
| 5,940,470 | A | * | 8/1999 | Palm-Plessmann et al. . 378/197 |
| 6,325,537 | B1 | * | 12/2001 | Watanabe .................... 378/197 |
| 6,463,121 | B1 | * | 10/2002 | Milnes ......................... 378/62 |
| 6,483,890 | B1 | * | 11/2002 | Malamud ..................... 378/22 |

* cited by examiner

Primary Examiner—Edward J. Glick
Assistant Examiner—Allen C. Ho
(74) Attorney, Agent, or Firm—Schiff & Hardin LLP

(57) ABSTRACT

A universal X-ray device has a movably suspended holder at which an X-ray radiator and a radiation detector are arranged, with the radiator being mounted so as to be pivotable around at least one axis perpendicular to the plane of the holder, and with the detector being displaceably mounted in the detector plane.

9 Claims, 6 Drawing Sheets

UNIVERSAL X-RAY DEVICE HAVING A PIVOTALLY MOUNTED RADIATOR AND A DISPLACEABLY MOUNTED DETECTOR

BACKGROUND OF THE INVENTION

1. Field of the Invention

The present invention is directed to a universal X-ray device of the type having a movably suspended holder, for example a C-arm, at which a radiator for generating X-rays and a detector for receiving the X-rays are arranged.

2. Description of the Prior Art

An X-ray device of this type is disclosed, for example, in U.S. Pat. No. 5,410,584, which has a first C-arm that carries a radiation emitter at one end and a radiation detector lying opposite. The first C-arm is carried by a further, second C-arm, so as to be adjustable along its circumference via a corresponding holder.

Over the course of time, different embodiments of devices have developed in X-ray technology for the various disciplines of X-ray based examination. Thus, there are specific devices for cardangiography, general angiography, surgery, stomach/intestinal diagnostics, pulmonary diagnostics, etc.

This specialization of the devices and the necessity of keeping a multitude of different devices on hand, which involves a considerable requirement for space as well as limiting the usage of the devices and thus their economic feasibility, have resulted in the introduction of universally employable systems. The use of universal systems also has been driven by the fact that overlaps increasingly occur even among the various medical disciplines, so that the specifically designed devices for the individual applications are often too specific and thus cannot be utilized optimally at all. In this context, the system costs, particularly the costs of specific components, for example the X-ray detector, play an important part.

For cost reasons, it is also desirable not to have a number of detectors of different sizes and different designs, as is often done, but to have only a few types of detectors insofar as possible and also to employ optimally small formats, since standardization is increasingly occurring in image systems and in image processing. For small detectors, however, there is the necessity of merging or combining individual images for obtaining larger-area exposures, for which projection distortions reportedly occur in the case of known devices. Heretofore, only relatively narrow image strips having a maximum image width of approximately 5 cm were combined in a "spine presentation", this in turn requiring a number of exposures, the examination time being lengthened and the device usage being reduced as a result.

SUMMARY OF THE INVENTION

An object of the present invention is to provide a universal X-ray device and a method for the operation of an X-ray device that can be unproblemmatically adapted to the various diagnostic purposes and that allow images of the detector registered next to one another to be combined error-free and undistorted to form a large image.

This object is achieved in accordance with the invention in an X-ray device wherein the radiator is mounted to a holder so as to be pivotable around at least one axis perpendicular to the plane of the holder, and that wherein the detector is displaceably mounted in the detector plane. Such an X-ray device can, for example, be constructed on the basis of a C-arm apparatus.

As a result of this mobility of the radiator and the detector at the holder, for example at the C-arm, which does not exist in conventional X-ray devices, a number of different application possibilities of such a universal X-ray device arise. The radiator is preferably pivotable toward the outside by at least 90° relative to the connecting line to the detector, so that an inventive device—in the position wherein the radiator is rotated out—also can be employed for exposures at a succinct type wall stand having an additional detector or film/storage foil.

In an embodiment of the invention, the radiator can be pivotable around a second axis lying in the plane of the holder, so as to be tiltable out of this plane. This two-axis pivotability can be realized by a Cardanic bearing of the radiator at the holder.

The displacement of the detector in its plane preferably is realized with the detector rotatably seated at a swivel arm that is rotatably hinged to an end of the holder such that it is displaceable in the detector plane.

The swivelling of the radiator as well as of the detector at the holder, as well as the swivelling and the displacement of the holder, preferably ensue via motorized actuators. This allows the advantageous possibility of implementing the movements of the holder, the detector and the radiator with a control unit connected thereto, so as that an error-free and undistorted combining of the images of the detector to form a large image can ensue.

The control unit can cause the combination of the radiator and detector to tilt around the rotational axis of the radiator. This does not in reality occur by a rotation and tilting of the radiator around its rotational axis, but by rotating the holder around its axis with a simultaneous displacement of the holder, so that a superimposition of the movements leads to the desired tilting around the rotational axis of the radiator. Separate adjustment of the radiator and of the detector is not required for this specific control in order to be able to merge a number of juxtaposed images without distortion.

The above object also is inventively achieved in a method wherein the detector is moved for the registration of a large-format, composite X-ray image so that it assumes exposure positions on a circular arc around the focus of the radiator, and wherein the X-ray beam of the radiator is directed onto the detector so that the central ray of the X-ray beam is perpendicularly incident on the middle of the detector.

It has proven advantageous for the detector to be displaced and aligned into the various exposure positions.

Advantageously, the radiator can be tilted or a primary radiation diaphragm can be adjusted for aligning the X-ray beam of the radiator onto the detector.

DESCRIPTION OF THE DRAWINGS

FIG. 4 is a perspective view of the inventive X-ray device with the radiator rotated out for exposures at the wall stand wherein.

DESCRIPTION OF THE PREFERRED EMBODIMENTS

Figure 1:
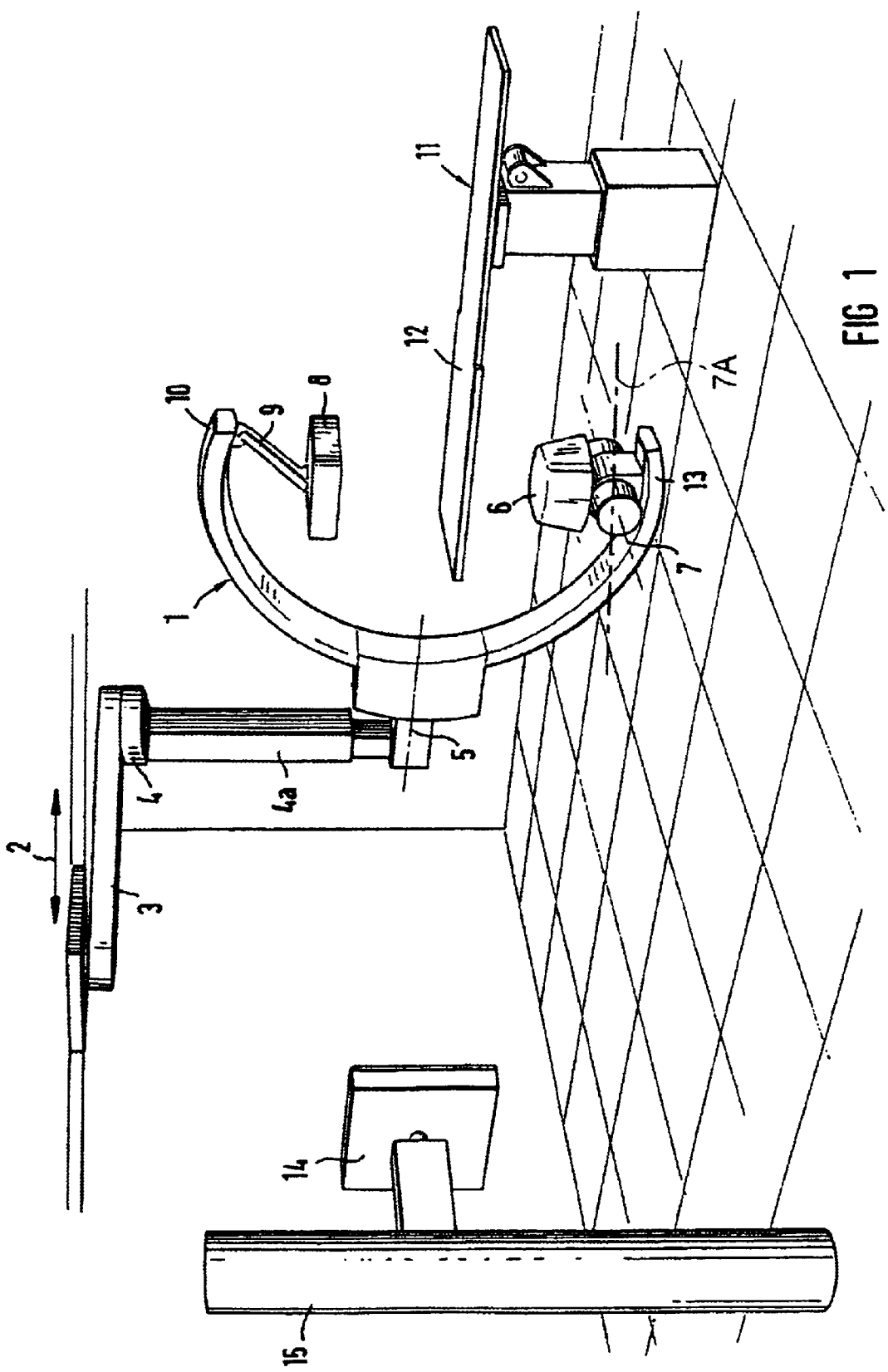
FIG. 1 is a perspective view of an inventive, universal X-ray device having an additional detector arranged next to the C-arm.

The inventive, universal X-ray device shown in FIG. 1 is fashioned as a ceiling mounted device, but it could be equally fashioned as a wall mounted device or a stand device. The C-arm 1, as a holder, also could be displaceably mounted at the ceiling in the direction of the double arrow 2. In the illustrated exemplary embodiment, however, a corresponding longitudinal motion is possible on the basis of a number of support arms 3, 4 and 4a that are rotationally articulated to one another. In any case, the standard swivel axis 5 is additionally provided in order to be able to swivel the C-arm 1 from the illustrated position through 90° into a horizontal attitude.

The inventive fashioning of the universal X-ray device produces several advantages. A radiator 6 for generating an X-ray beam can be swivelled around an axis 7 proceeding perpendicularly to the plane of the C-arm 1. The radiation detector 8 can be, for example a-Si solid state image transducer or an X-ray image intensifier coupled to a video camera or a storage luminafore foil or a film, and is also displaceable in its detector plane. This is achieved in the illustrated exemplary embodiment by a swivelable bearing of the support arm 9 that is correspondingly mounted both at the housing of the detector 8 as well as at the end 10 of the C-arm. A standard, support table 11 has a bearing plate 12 that can be displaceable to an upright position as is required for the application in FIG. 3. In addition to the swivability of the radiator 6 around the axis 7, an additional swivel can be provided around a further axis perpendicular thereto or, as warranted, a Cardanic suspension of the radiator 6 can be provided at the lower end 13 of the C-arm 1. Axis 7a is illustrated as an example of such a further axis. An additional detector 14 is arranged at a column 15 that is required for a functional transillumination device that is also adjustable with the inventive X-ray device, as shown in detail in FIG. 4.

Figure 2:
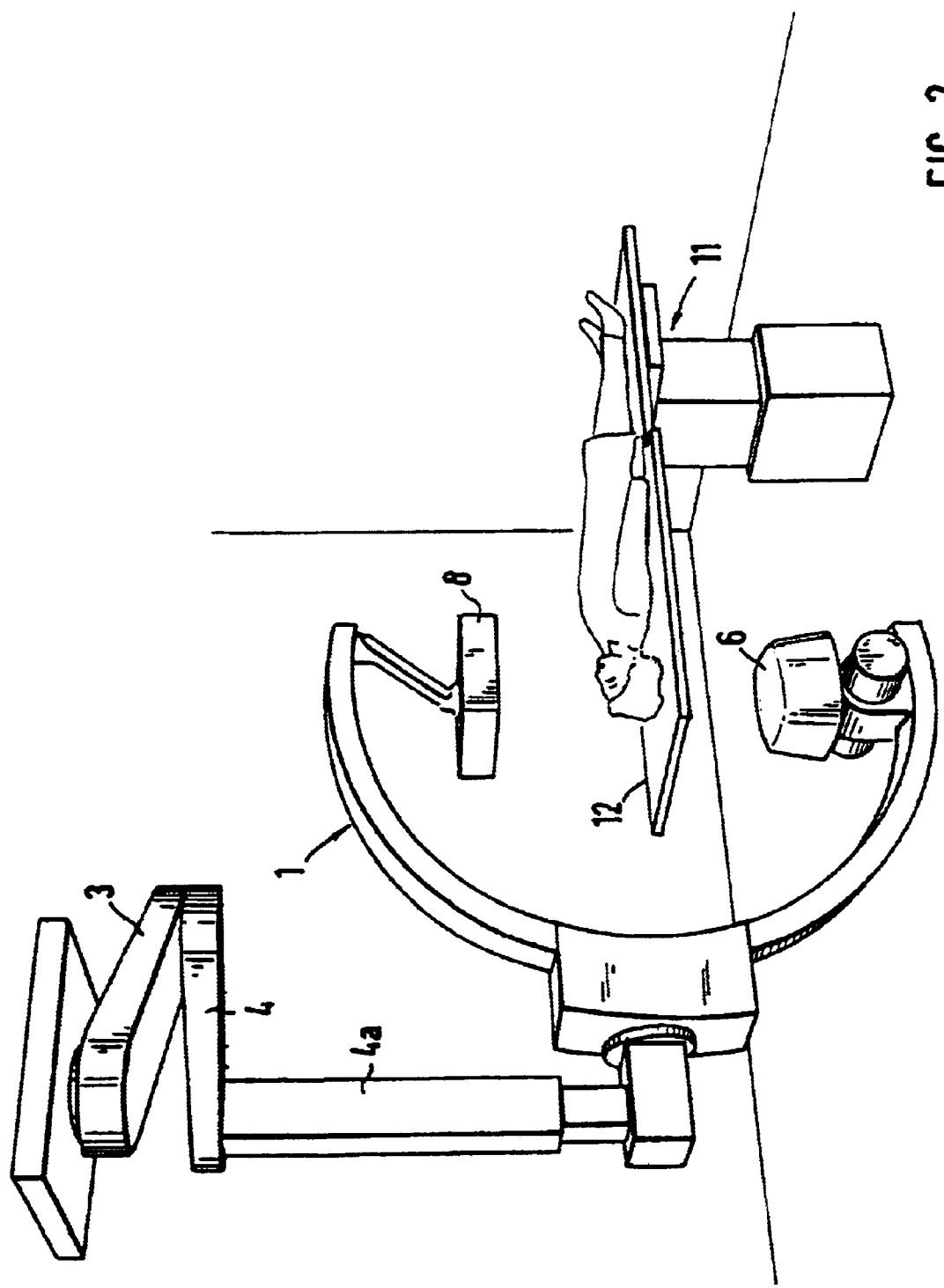
FIG. 2 is a perspective view of the inventive universal X-ray device with the detector in the position wherein it is swivelled in for employment of the system with an isocenter.

FIG. 2 shows a position of the inventive X-ray device already selected in the overview of FIG. 1 having the detector 8 swivelled in, as it must be positioned for employment of the system with an isocenter.

Figure 3:
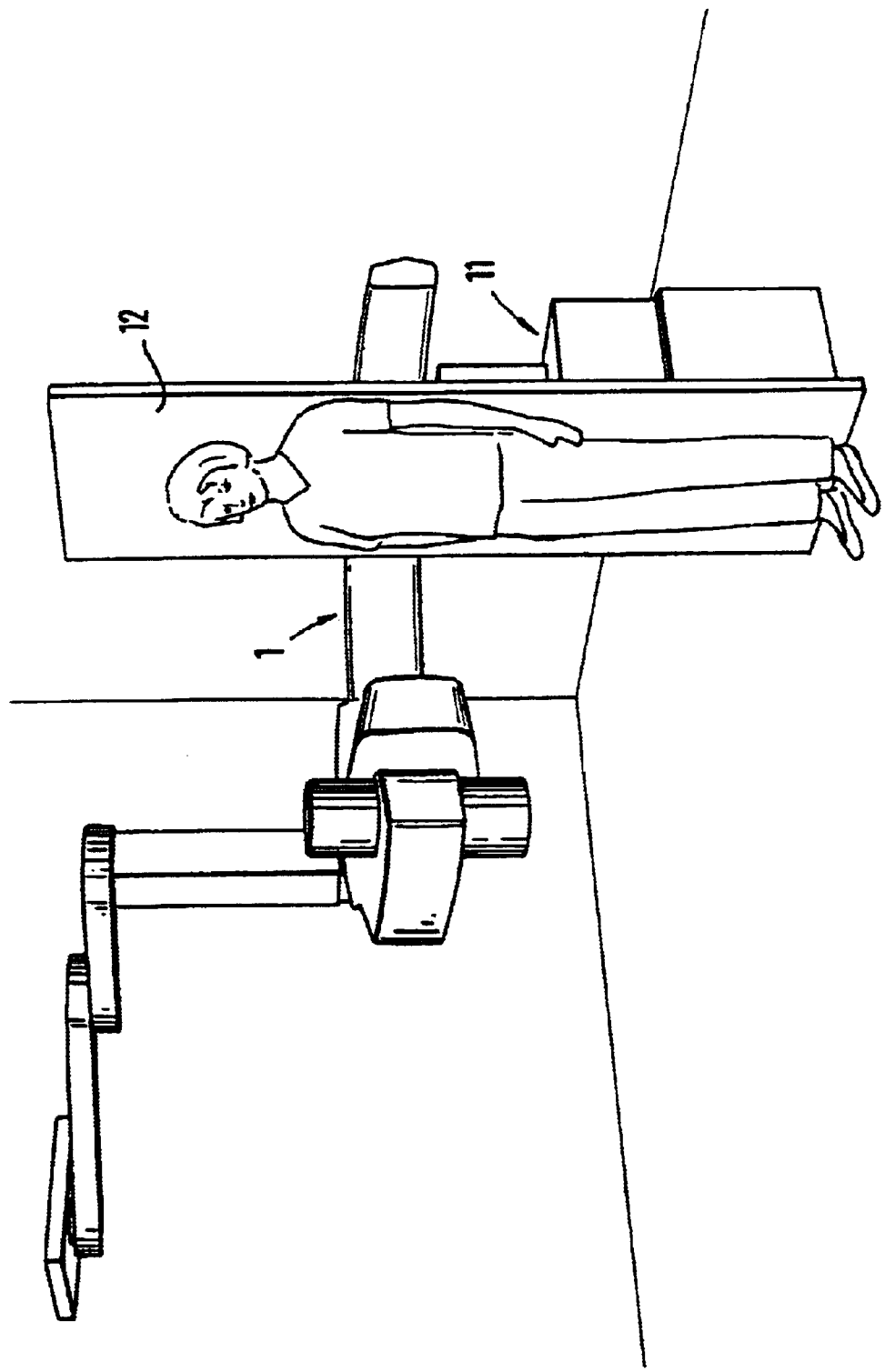
FIG. 3 is a perspective view of the X-ray device for a diagnostic application with the table displaced to an upright position.

FIG. 3 shows the inventive X-ray device with horizontally swivelled C-arm 1 for a diagnostic application with an upright table plate 12 of the patient support table 11.

Figure 4:
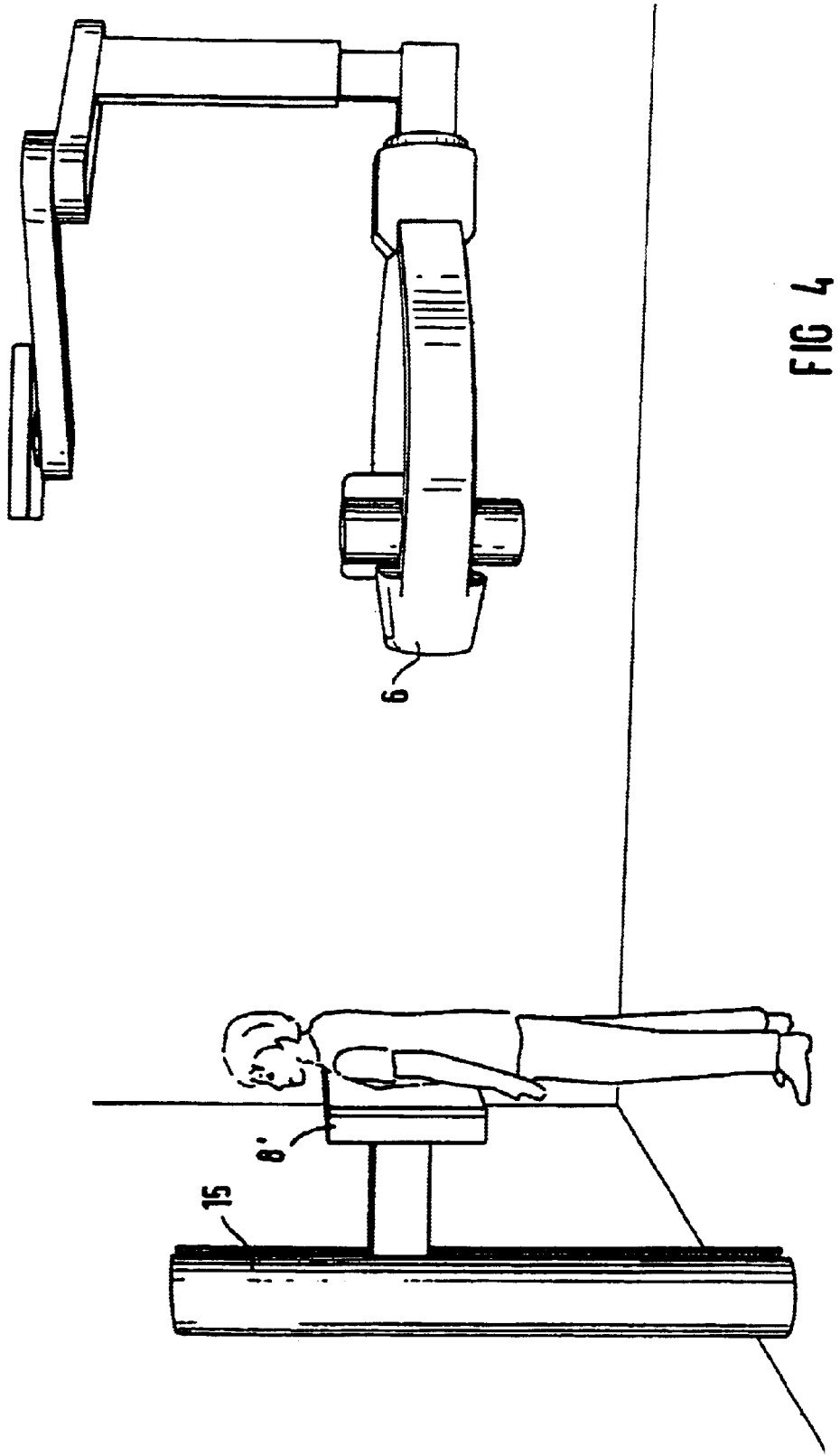

In FIG. 4, the radiator 6 is rotated out toward the front by 90° out of the plane of the C-arm, i.e. by 90° around the axis 7 in FIG. 1 in the clockwise direction, in order to be able to implement exposures at the raster wall stand 15 with an additional detector 8', or with a film or a storage foil as well.

Figure 5:
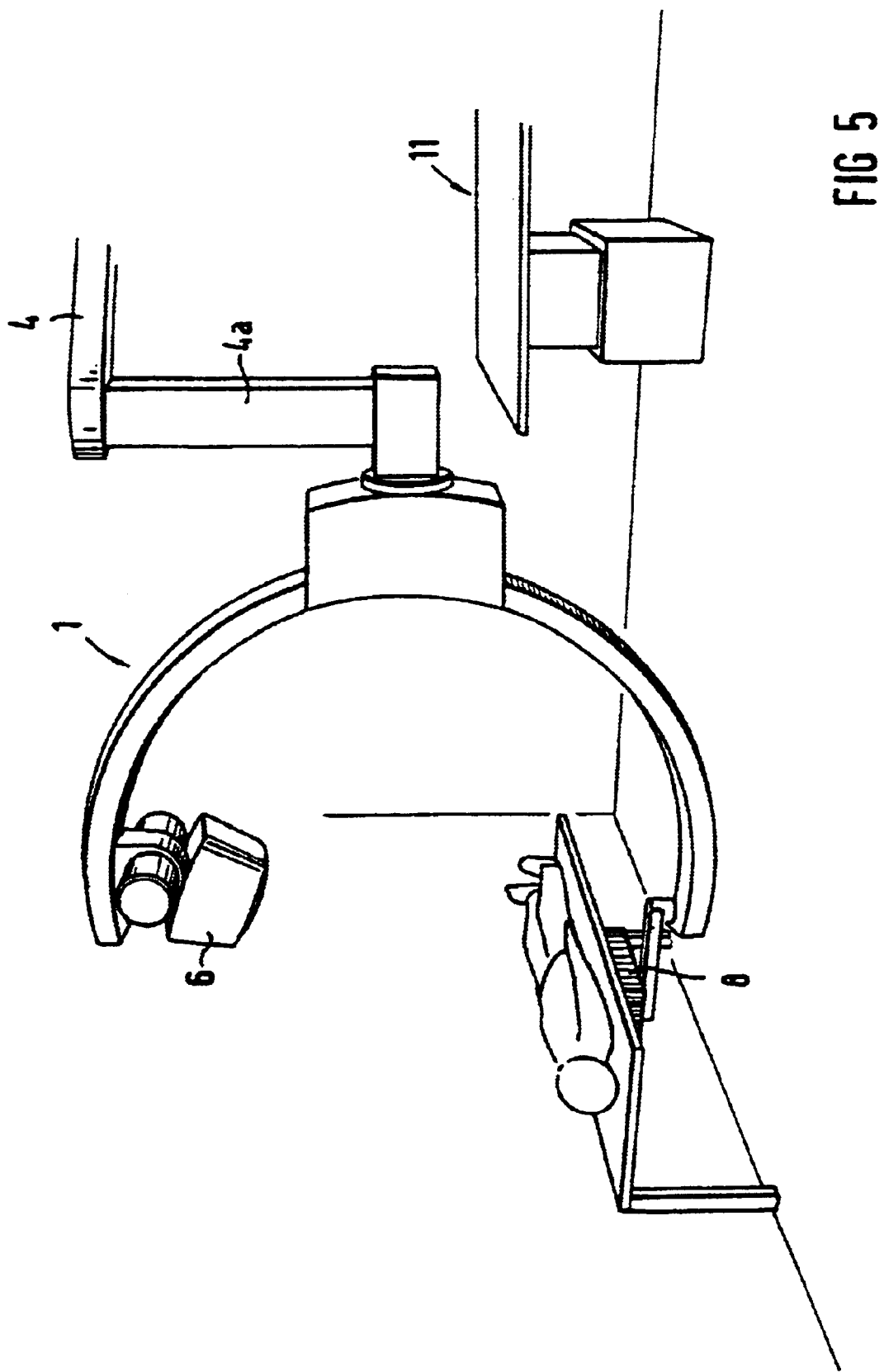
FIG. 5 is a perspective view of the inventive X-ray device with the detector swivelled out for exposures or transilluminations at a freely movable table or bed.

FIG. 5 shows an arrangement of the inventive universal X-ray device wherein the detector 8 is swivelled outward by 180° from the position according to FIG. 1 in order to be able implement exposures or transilluminations at a freely movable table or bed. Here, it is especially the extremely small structural height of the detector arrangement of a solid-state image transducer that is advantageous. Due to the versatile swivability and adjustability of the C-arm 1, the exposure or transillumination can ensue at a table or bed next to the actual patient table 11, as indicated in FIG. 5.

Figure 6:
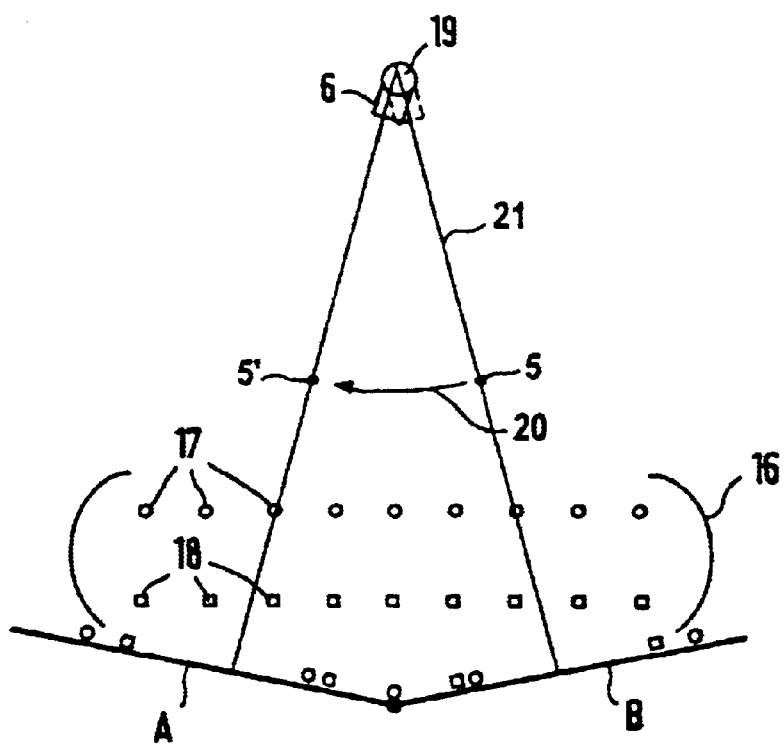
FIG. 6 is a schematic illustration of the beam path given a specific control of the X-ray device wherein the radiator and detector tilt as a unit around the rotational axis of the radiator in order to be able to combined juxtaposed images without distortion.
Figure 7:
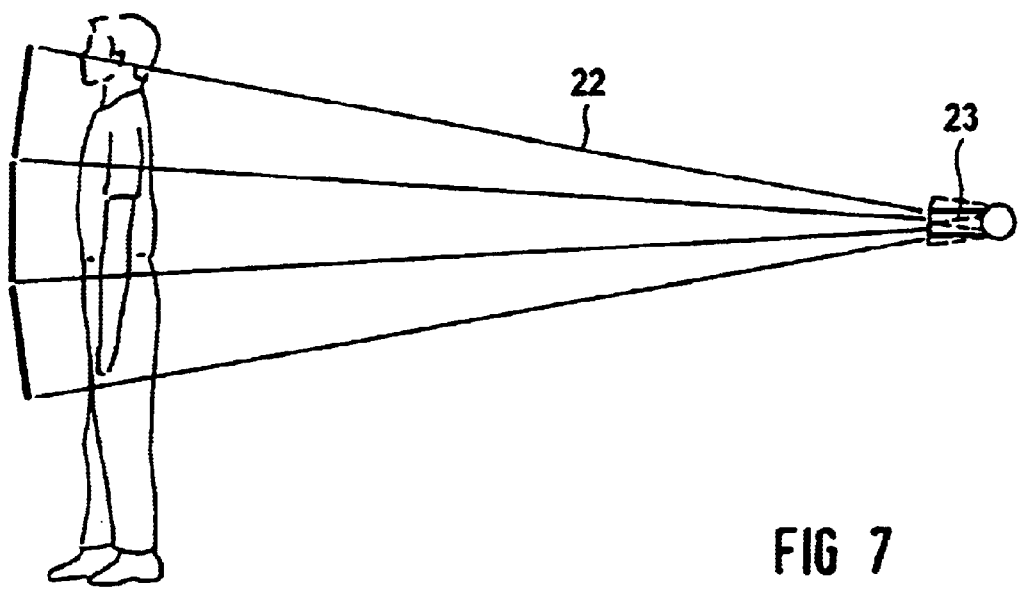
FIG. 7 is a schematic illustration of the application of the tilting method according to FIG. 6 for combining a number of images, for example for a "spine presentation".

FIG. 6 schematically shows the beam guidance for achieving a composite X-ray image from two smaller images. The patient 16 is merely shown on the basis of a few round dots 17 or box-shaped dots 18 in order to illustrate how a distortion-free merging of the two images A and B to form a correspondingly larger image is possible on the basis of the specific swiveling of the device. Inventively, a superimposition of the swivel motion of the C-arm 1 around its rotational axis 5 ensues in combination with a transverse displacement of C-arm 1, so that the rotational axis 5 is displaced from its position 5 into the position 5' in the direction of the arrow 20. Without having to individually move the radiator 6 or the detector 8 relative to the C-arm 1 for generating the image A or B swivelling of the radiator 6 and the detector 8 as a unit ensues around the focus 19 of the radiator 6, so the central ray 21 is always perpendicularly directed onto the middle of the detector 8. As a result of this specific tilting, for example, a "spine presentation" can be achieved by merging three exposures, as schematically shown in FIG. 7.

It is self-evident that a number of exposures can be combined not only in one direction but in the other direction as well. By a corresponding control of the swivel motions of the support arms 3, 4 and 4a, a tilting around the focus of the radiator 6 also can be achieved in this direction.

The adjustment into the various exposure positions for generating the two images A and B for a large-format, composite X-ray image also can be achieved by moving the detector 8 into the respective exposure positions with the support arm 9, the exposure positions lying on a circular arc around the focus 19 of the radiator 6. The detector 8 is thereby aligned such that the central ray 21 of the X-ray beam 22 is vertically incident on the middle of the detector 8. For swiveling the X-ray beam 22, either the radiator 6 can be tilted around its focus 19 or the primary radiation diaphragm 23 of the radiator 6 can be adjusted by shifting its lamellae.

Although modifications and changes may be suggested by those skilled in the art, it is in the intention of the inventor to embody within the patent warranted hereon all changes and modifications as reasonably and properly come within the scope of his contribution to the art.

I claim as my invention:

1. A universal X-ray device comprising:
   an X-ray radiator;
   a radiation detector for detecting X-rays emitted by said radiator;
   a movably suspended holder having a holder plane;
   a radiator mount for mounting said radiator to said holder so that said radiator is rotatable around at least one axis perpendicular to said holder plane and around a second axis disposed in said holder plane, allowing said radiator to be tilted out of said holder plane; and
   a detector mount for mounting said detector to said holder allowing displacement of said detector in a detector plane.

2. A universal X-ray device as claimed in claim 1 wherein said holder is a C-arm.

3. A universal X-ray device as claimed in claim 1 wherein said radiator mount allow said radiator to be rotated by at least 90° away from a line proceeding between said radiator and said detector.

4. A universal X-ray device as claimed in claim 1 wherein said radiator mount is a Cardanic mount.

5. A universal X-ray device as claimed in claim 1 wherein said detector mount is a swivel arm having a first end to which said detector is rotatably mounted and a second end that is rotatably hinged to an end of said holder so that said arm is displaceable in said detector plane.

6. A universal X-ray device as claimed in claim 1 further comprising a first motor actuator for rotating said radiator, a second motor actuator for displacing said detector, and a third motor actuator for moving said holder.

7. A universal X-ray device as claimed in claim 6 further comprising a control unit connected to said first motor actuator, said second motor actuator and said third motor actuator for controlling respective movements of said holder, said detector and said radiator to obtain a plurality of individual images for undistorted combination to form a larger, combined image.

8. A universal X-ray device as claimed in claim 7 wherein said radiator has a focus from which said radiation is emitted, and wherein said control unit tilts said radiator and said detector as a unit relative to said focus.

9. A universal X-ray device as claimed in claim 7 wherein said radiator has a focus from which said radiation is emitted, and wherein said control unit tilts said radiator and said detector as a unit relative to said focus.

* * * * *